US012714433B2

(12) United States Patent
Porter et al.

(10) Patent No.: US 12,714,433 B2
(45) Date of Patent: Aug. 25, 2026

(54) EMBOLIC DEVICES AND METHODS OF MANUFACTURING SAME

(71) Applicants: STRYKER CORPORATION, Kalamazoo, MI (US); STRYKER EUROPEAN OPERATIONS LIMITED, Carrigtwohill (IE)

(72) Inventors: Stephen Porter, Piedmont, CA (US); Andrew S. Lee, San Jose, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 400 days.

(21) Appl. No.: 18/487,939

(22) Filed: Oct. 16, 2023

(65) Prior Publication Data

US 2024/0032938 A1 Feb. 1, 2024

Related U.S. Application Data

(63) Continuation of application No. 16/989,532, filed on Aug. 10, 2020, now Pat. No. 11,819,217, which is a (Continued)

(51) Int. Cl.

*A61B 17/12* (2006.01)
*A61F 2/86* (2013.01)

(Continued)

(52) U.S. Cl.

CPC .. *A61B 17/12145* (2013.01); *A61B 17/12031* (2013.01); *A61B 17/12113* (2013.01);

(Continued)

(58) Field of Classification Search

CPC ...... B21F 1/04; B21F 3/00; B21F 7/00; B21F 45/008

(Continued)

(56) References Cited

U.S. PATENT DOCUMENTS

| | | | |
|---|---|---|---|
| 6,322,576 B1 | 11/2001 | Wallace et al. | |
| 6,616,617 B1 * | 9/2003 | Ferrera ............ | A61B 17/12113 600/585 |

(Continued)

FOREIGN PATENT DOCUMENTS

| | | |
|---|---|---|
| EP | 1698284 | 9/2006 |
| JP | 2001-513389 A | 9/2001 |

(Continued)

OTHER PUBLICATIONS

Extended European Search Report for EP Patent Appln. No. 22165087.2 dated Jun. 23, 2022.

(Continued)

*Primary Examiner* — Edward T Tolan

(74) *Attorney, Agent, or Firm* — Vista IP Law Group, LLP

(57) ABSTRACT

A flat embolic braid having a first side comprising a first side surface, and a second side comprising a second side surface facing in an opposite direction than the first side surface, the braid having an elongated constrained configuration for being deployed through a delivery catheter, and a three-dimensional unconstrained configuration, wherein in the three-dimensional unconstrained configuration, the braid assumes a plurality of successive loops in which the braid is at least partially twisted between successive loops of the plurality, so that the first side surface faces externally of each loop, and the second side surface faces an interior of each loop, respectively, regardless of a change in direction and/or orientation of the braid.

20 Claims, 6 Drawing Sheets

Related U.S. Application Data continuation-in-part of application No. 15/393,037, filed on Dec. 28, 2016, now Pat. No. 10,743,883.

(60) Provisional application No. 62/272,907, filed on Dec. 30, 2015.

(51) Int. Cl.

| | |
|---|---|
| ***B21F 3/00*** | (2006.01) |
| ***B21F 45/00*** | (2006.01) |
| *A61B 17/00* | (2006.01) |
| *A61F 2/82* | (2013.01) |

(52) U.S. Cl.

CPC .... *A61B 17/1214* (2013.01); *A61B 17/12172* (2013.01); *A61F 2/86* (2013.01); *B21F 3/00* (2013.01); *B21F 45/008* (2013.01); *A61B 2017/00526* (2013.01); *A61B 2017/00862* (2013.01); *A61B 2017/00867* (2013.01); *A61B 2017/00893* (2013.01); *A61B 2017/1205* (2013.01); *A61F 2002/823* (2013.01); *A61F 2220/005* (2013.01)

(58) Field of Classification Search

USPC .................................... 140/92.1, 102, 102.5

See application file for complete search history.

(56) References Cited

U.S. PATENT DOCUMENTS

| | | | | |
|---|---|---|---|---|
| 6,635,069 | B1 * | 10/2003 | Teoh | A61B 17/1215 606/198 |
| 6,712,835 | B2 * | 3/2004 | Mazzocchi | A61F 2/0105 606/110 |
| 7,488,332 | B2 * | 2/2009 | Teoh | A61B 17/12113 606/113 |
| 8,066,036 | B2 * | 11/2011 | Monetti | A61B 17/1219 140/71 C |
| 8,801,747 | B2 * | 8/2014 | Strauss | A61B 17/12022 606/200 |
| 8,910,501 | B2 * | 12/2014 | Gorospe | A61B 17/12109 140/71 C |
| 9,089,405 | B1 * | 7/2015 | Gulachenski | A61B 17/12113 |
| 9,155,643 | B2 * | 10/2015 | Clerc | D04C 1/06 |
| 9,713,475 | B2 * | 7/2017 | Divino | A61B 17/12172 |
| 10,299,798 | B2 * | 5/2019 | Le | A61B 17/12113 |
| 10,709,453 | B2 * | 7/2020 | Suzuki | A61B 17/12113 |
| 2002/0120297 | A1 | 8/2002 | Shadduck | |
| 2007/0225738 | A1 | 9/2007 | Pal | |
| 2009/0054965 | A1 | 2/2009 | Richard | |
| 2012/0239074 | A1 * | 9/2012 | Aboytes | A61B 17/12145 606/191 |
| 2013/0116722 | A1 | 5/2013 | Aboytes et al. | |
| 2013/0184658 | A1 | 7/2013 | Duncan | |
| 2015/0182227 | A1 | 7/2015 | Le et al. | |
| 2017/0224355 | A1 * | 8/2017 | Bowman | A61B 17/1214 |

FOREIGN PATENT DOCUMENTS

| | | | |
|---|---|---|---|
| JP | 2004-511293 | A | 4/2004 |
| JP | 2010-521232 | A | 6/2010 |
| JP | 2013-537069 | A | 3/2012 |
| WO | WO 99/09893 | A1 | 3/1999 |
| WO | WO 02/32325 | A1 | 4/2004 |
| WO | WO 2008/112436 | A2 | 9/2008 |
| WO | WO 2008/112436 | A3 | 11/2008 |
| WO | WO 2011119872 | A1 | 9/2011 |
| WO | WO 2012/034135 | | 3/2012 |
| WO | WO 2014/144980 | A1 | 9/2014 |
| WO | WO 2015/184075 | A1 | 12/2015 |

OTHER PUBLICATIONS

Foreign Search Report for CN Patent Appln. No. 201680074865X dated Aug. 3, 2021.

Foreign OA for CN Patent Appln. No. 201680074865X dated Aug. 9, 2021.

English translation for OA and Search Report for CN Patent Appln. No. 201680074865X.

Foreign Office Action for JP Patent Appln. No. 2018-530734 dated Oct. 1, 2020.

Office Action dated Apr. 26, 2022 for Japanese Patent Application No. 2021-094933.

Foreign Office Action and Search Report for CN Patent Appln. No. 201680074865X dated Sep. 3, 2020.

Foreign OA and search report for CN Patent Appln. No. 2022105349263 dated Mar. 2024 (with English translation).

* cited by examiner

EMBOLIC DEVICES AND METHODS OF MANUFACTURING SAME

RELATED APPLICATION DATA

The present application is a continuation of U.S. patent application Ser. No. 16/989,532, filed Aug. 10, 2020, which is a continuation-in-part of U.S. patent application Ser. No. 15/393,037, filed Dec. 28, 2016, now U.S. Pat. No. 10,743, 883, issued on Aug. 18, 2020, which claims the benefit under 35 U.S.C. § 119 to U.S. provisional patent application Ser. No. 62/272,907, filed Dec. 30, 2015. The contents of the aforementioned application(s) are hereby incorporated herein by reference in their entirety as if set forth fully herein, and the benefit of priority to each of the aforementioned applications is hereby expressly claimed in accordance with 35 U.S.C. §§ 119, 120, 365, 371 and/or any other applicable statutes.

FIELD OF THE INVENTION

The inventions disclosed herein relate to embolic devices. More particularly, the present disclosure pertains to methods of manufacturing embolic devices.

BACKGROUND

Medical devices such as coils, tubular mesh elements and other expandable members, collectively referred to hereinafter as "embolic devices," are often utilized for treating various types of vascular defects, particularly, aneurysms. Aneurysms are localized, blood-filled dilation of a blood vessel caused by disease, blood flow/pressure exerted in the vessel and/or weakening of the vessel wall. Aneurysm usually assumes a sac or balloon-like configuration that extends from a blood vessel. Aneurysm can rupture and cause hemorrhage, stroke (e.g., intracranial aneurysm) and other damaging consequences to the patient. During the treatment of an aneurysm, an embolic device is loaded onto a delivery system in a collapsed or radially compressed delivery configuration and then introduced into an aneurysm sac. Once delivered within the aneurysm sac, the embolic device may then expand or be expanded to an expanded configuration filling and occluding the aneurysm. Embolic devices may have a variety of sizes and shapes; however, embolic devices for treatment of aneurysm usually assume a spherical secondary configuration when deployed within the aneurysm sac. When implanted within the sac, the embolic device may further reinforce the inner walls of the aneurysm sac while occluding the aneurysm, reducing the probability of rupture or preventing further rupture of the aneurysm.

Embolic devices are commonly composed of self-expanding materials, so that when the devices are deployed from the delivery system into the target location in a patient; the unconstrained devices expand without requiring assistance. Self-expanding embolic devices may be biased so as to expand upon release from the delivery catheter and/or include a shape-memory component which allows the device to expand upon exposure to a predetermined condition. Some embolic devices may be characterized as hybrid devices which have some characteristics of both self-expandable materials and non-self-expandable materials.

Embolic devices can be made from a variety of materials, including polymers (e.g., nonbioerodable and bioerodable plastics) and metals. Bioerodable polymer embolic devices are desirable for some applications due to their biodegradeability and generally increased flexibility compared to metal embolic devices. Embolic devices can be made from shape memory or superelastic materials, such as shape memory metals (e.g., shape memory Nitinol) and polymers (e.g., polyurethane). Such shape memory embolic devices can be induced (e.g., by temperature, electrical or magnetic field or light) to take on a shape (e.g., a radially expanded shape) after delivery to a treatment site. Superelastic embolic materials, such as superelastic Nitinol, take on a shape after delivery without need for an inductive stimulus. Other devices materials include stainless steel, platinum, and Elgiloy. In drug delivery embolic devices, the device can carry and/or the surface of the device can be coated with a bioactive or therapeutic agent (e.g., thrombosis inducing agent).

Commonly used embolic devices are helical wire coil having windings dimensioned to engage the walls of the aneurysm. Although, embolic coils may migrate out of an aneurysm sac, particularly when delivered in wide neck aneurysm.

Some exemplary embolic coils are described, for instance, in U.S. Pat. No. 4,994,069, which discloses an embolic coil that assumes a linear helical configuration when stretched and a folded, convoluted configuration when relaxed. The stretched configuration is used in placing the coil at the target site (by its passage through a delivery catheter) and the coil assumes a convoluted relaxed configuration once the device is deployed at the target site. The '069 patent discloses a variety of secondary shapes of the embolic coils when deployed at the target site, such as "flower" shapes, double vortices, and random convoluted shapes. Other three-dimensional embolic coils have been described in U.S. Pat. No. 5,624,461 (i.e., three-dimensional in-filling embolic coil), U.S. Pat. No. 5,639,277 (i.e., embolic coils having twisted helical shapes) and U.S. Pat. No. 5,649,949 (i.e., variable cross-section conical embolic coils). Embolic coils having little or no inherent secondary shape have also been described, such as in U.S. Pat. Nos. 5,690,666 and 5,826, 587.

Spherical shaped embolic devices are described in U.S. Pat. No. 5,645,558, which discloses that one or more strands can be wound to form a substantially hollow spherical or ovoid shape comprising overlapping strands when deployed in an aneurysm. Other embolic devices that assume spherical shapes when deployed are described in U.S. Pat. No. 8,998,947, which discloses tubular mesh having petal-like sections to form a substantially spherical shape having overlapping petals-like sections when deployed in an aneurysm.

A variety of delivery assemblies for embolic devices are known. For instance, U.S. Pat. No. 5,250,071 (i.e., interlocking clasps), U.S. Pat. No. 5,312,415 (i.e., interconnecting guidewire to deliver multiple coils), and U.S. Pat. Nos. 5,354,295 and 6,425,893, to Guglielmi (i.e., electrolytic detachment).

SUMMARY

In an exemplary embodiment of the disclosed inventions, an embolic device is formed out of an elongate flat member having a longitudinal axis, a first side comprising a first side surface, and a second side comprising a second side surface, the first and second sides being reverse to each other with the first side surface and second side surface facing in opposite directions. The elongate flat member has an elongated constrained configuration for being deployed through a delivery catheter to targeted vascular site, and a three-dimensional unconstrained configuration, wherein in the three-dimensional unconstrained configuration, the elongate flat member assumes a plurality of successive loops in which the elongate flat member is at least partially twisted about its longitudinal axis between each loop of the plurality, so that the first side surface faces externally of each loop, and the second side surface faces an interior of each loop, respectively, regardless of a change in direction and/or orientation of the elongate flat member.

Without limitation, the elongate flat member may be a braid formed out of one or more braid members, wherein the one or more braid members are metallic filaments or wires. For example, the elongate flat member may be a flattened tubular braid or a single layer, flat ribbon braid.

In an exemplary embodiment, the three-dimensional unconstrained configuration is imparted on the elongate flat member by thermally treating the elongate flat member while the elongate flat member is wound in alternating directions about respective posts extending outwardly from a mandrel to thereby form the plurality of successive loops. In a preferred embodiment, the plurality of successive loops include at least a first loop defining a first plane, a second loop defining a second plane that is not coplanar with the first plane, and a third loop defining a third plane that is not coplanar with either of the first and second planes. In one exemplary embodiment, the plurality of successive loops comprising at least five successive loops.

In a more particular exemplary embodiment, an embolic device is provided for occluding an aneurysm, the embolic device comprising an elongate flat braid formed out of one or more metallic braid filaments or wires and having a longitudinal axis, a first side comprising a first side surface, and a second side comprising a second side surface, the first and second sides being reverse to each other with the first side surface and second side surface facing in opposite directions. The elongate flat braid has an elongated constrained configuration for being deployed through a delivery catheter into the aneurysm, and a three-dimensional unconstrained configuration after being deployed out of the delivery catheter within the aneurysm, wherein in the three-dimensional unconstrained configuration, the elongate flat braid assumes a plurality of successive loops in which the elongate flat braid is at least partially twisted about its longitudinal axis between each loop of the plurality, so that the first side surface faces externally of each loop towards an interior wall of the aneurysm, and the second side surface faces an interior of each loop, respectively, regardless of a change in direction and/or orientation of the elongate flat braid.

By way of example, the elongate flat braid may be a flattened tubular braid, or a single layer, flat ribbon braid, wherein the three-dimensional unconstrained configuration is imparted on the elongate flat braid by thermally treating the elongate flat braid while the elongate flat braid is wound in alternating directions about respective posts extending outwardly from a mandrel to thereby form the plurality of successive loops. The plurality of successive loops preferably include at least three successive loops, including a first loop defining a first plane, a second loop defining a second plane that is not coplanar with the first plane, and a third loop defining a third plane that is not coplanar with either of the first and second planes. In one embodiment, the plurality of successive loops includes at least five successive loops.

Other and further aspects and features of embodiments will become apparent from the ensuing detailed description in view of the accompanying figures.

DETAILED DESCRIPTION OF THE ILLUSTRATED EMBODIMENTS

Figure 1:
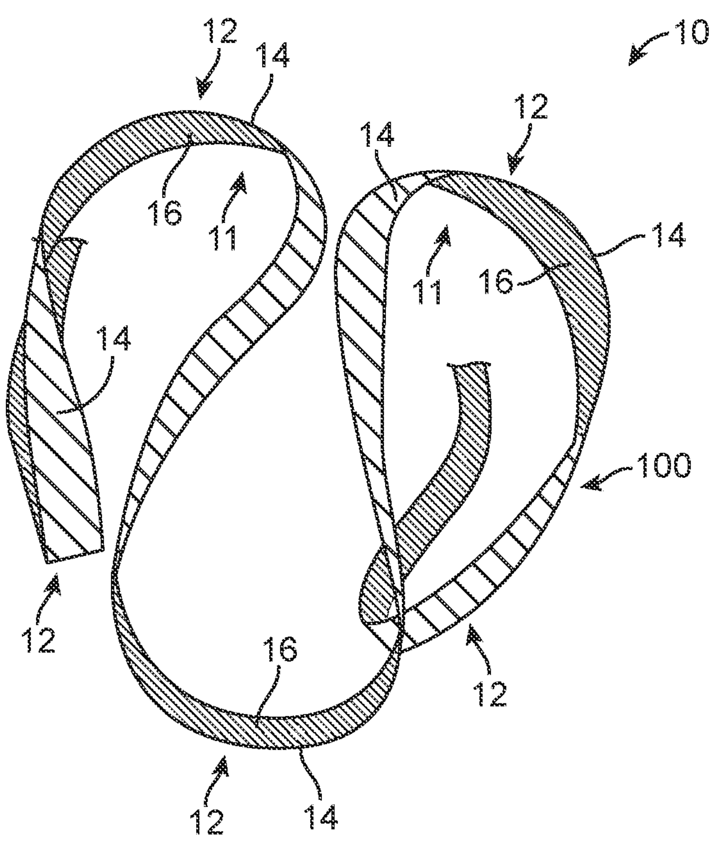
FIG. 1 is a perspective view of an embolic device manufactured according embodiments of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 2A:
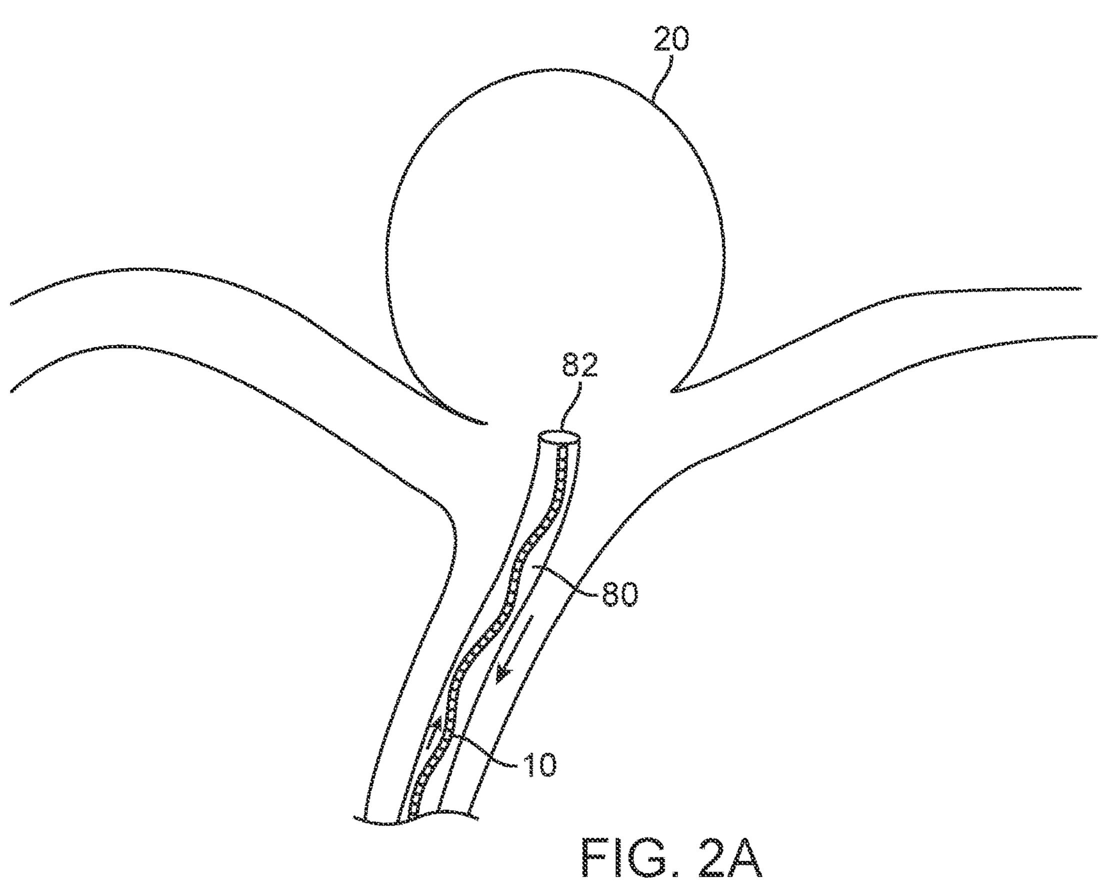
FIGS. 2A-B are cross-sectional views of delivery and deployed configurations of the embolic device of FIG. 1 at a target site, according embodiments of the disclosed inventions.
Figure 2B:
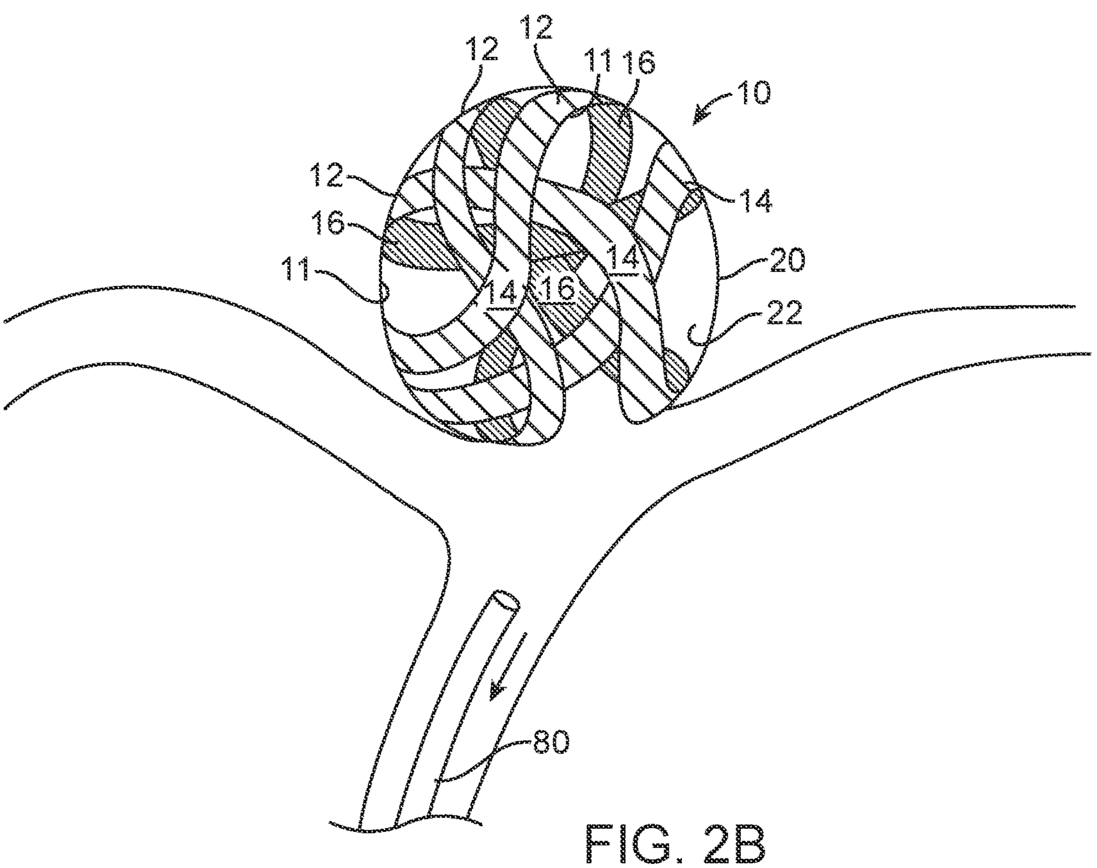

FIG. 1 illustrates an embolic device 10, according to the embodiments of the disclosed inventions. The embolic device 10 comprises an elongated constrained configuration (FIG. 2A) for being deployed through a delivery catheter 80 to targeted vascular site 20 (e.g., aneurysm sac). The embolic device 10 further comprises a three-dimensional unconstrained configuration (FIGS. 1 and 2B), in which the device 10 assumes a plurality of successive loops 12. For example, the device three-dimensional unconstrained configuration is assumed after the device 10 is advanced out of a distal opening 82 of the delivery catheter 80, and/or the delivery catheter 80 is withdrawn proximally relative to the embolic device 10 (or some of each) into the targeted vascular site 20 (FIG. 2B). The three-dimensional unconstrained configuration is set by applying a series of manufacturing steps to an elongate flat member 100 to include successive loops 12 in which the elongate flat member 100 is at least partially twisted about its longitudinal axis between each loop of the plurality, so that a first side surface 14 faces externally of each loop 12 towards an interior wall 22 of the aneurysm 20, and a second side surface 16 faces an interior 11 of each loop 12, respectively, regardless of a change in direction and/or orientation of the elongate flat member 100 (FIGS. 1, 2B). The plurality of successive loops 12 may include a first loop defining a first plane, a second loop defining a second plane that is not coplanar with the first plane, and a third loop defining a third plane that is not coplanar with either of the first and second planes, as shown in FIGS. 1 and 2B. In some embodiments, the plurality of successive loops comprises at least five successive loops 12, as shown in FIG. 2B.

The application of the series of manufacturing steps to the elongate flat member 100 for setting the three-dimensional unconstrained configuration of the embolic device 10 will be described in further detail below.

Figures 3A, 3B, 4A, 4B, 5A, 5B, 5C, 6A, 6B, 6C, 7A, 7B, 8A, 8B:
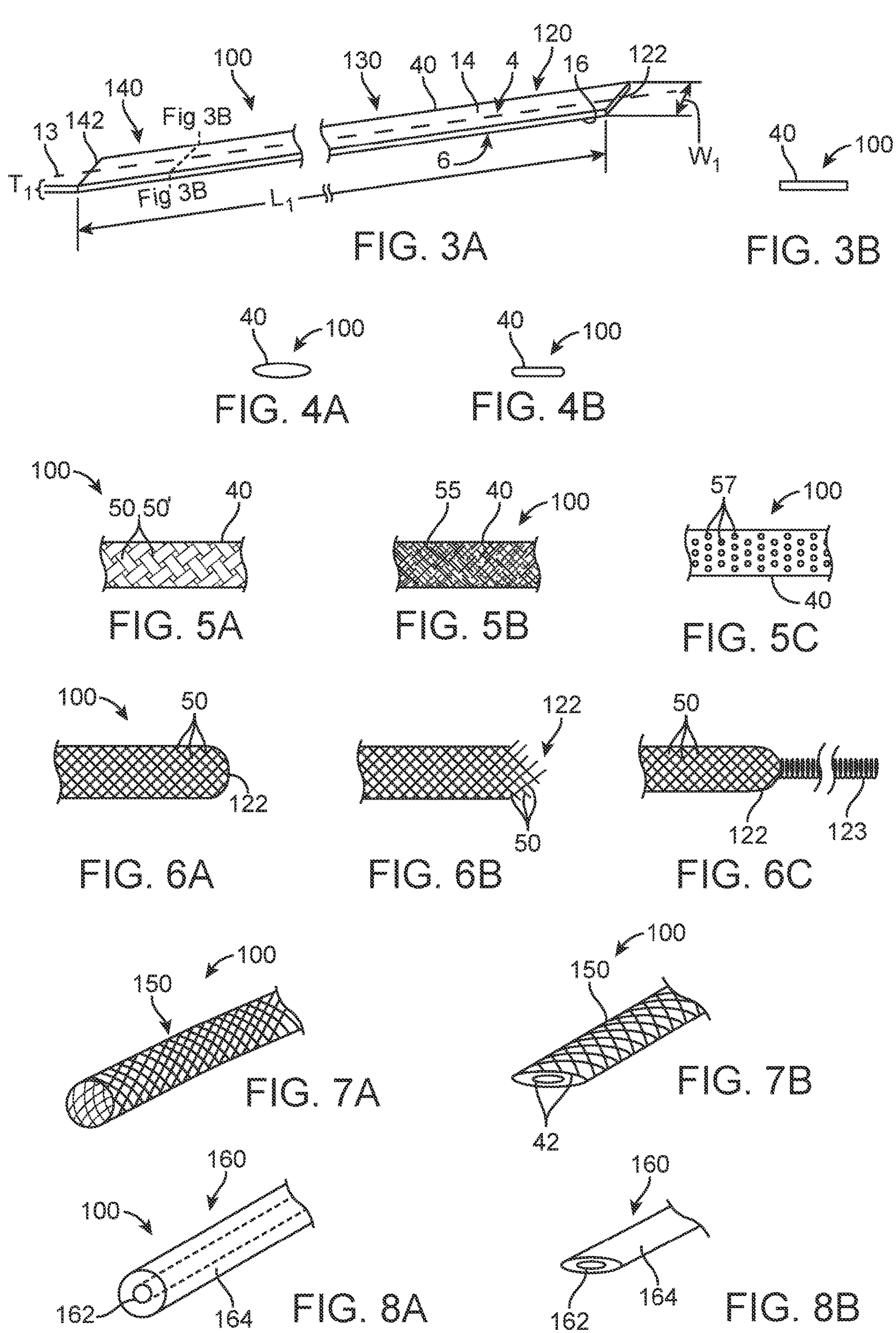
FIGS. 3A-B are perspective and cross-sectional views of an elongate flat member for the manufacturing of the embolic device of FIG. 1, according embodiments of the disclosed inventions.
FIGS. 4A-B are cross-sectional views of the elongate flat member of FIG. 3A, according other embodiment of the disclosed inventions.
FIGS. 5A-C are side views elongate flat members, according to other embodiments of the disclosed inventions.
FIGS. 6A-C are side views of end portions of the embodiment of FIG. 5B, according to embodiments of the disclosed inventions.
FIGS. 7A-B are perspective views of an elongate flat member, according to another embodiment of the disclosed inventions.
FIGS. 8A-B are perspective views of an elongate flat member, according to yet another embodiment of the disclosed inventions.

The elongate flat member 100 forming the embolic device 10 has a proximal portion 140, a middle portion 130 and distal portion 120, as shown in FIG. 3A. The proximal portion 140 includes a proximal end 142, and the distal portion 120 includes a distal end 122. The elongate flat member 100 comprises a ribbon-like configuration having a rectangular cross-section, as shown in FIGS. 3A and 3B. Alternative, the elongate flat member 100 may have any other suitable cross-sections, as for example: an ovoid or elliptical (FIG. 4A), flattened with rounded edges (FIG. 4B), flattened tubular (FIG. 7B) cross-section or the like, or combinations thereof. The elongate flat member 100 further comprises a longitudinal axis 13, a first side 4 comprising a first side surface 14, and a second side 6 comprising a second side surface 16, the first and second sides 4 and 6 being reverse to each other with the first side surface 14 and second side surface 16 facing in opposite directions, as shown in FIG. 3A.

For ease in illustration, the elongate flat member 100 shown in FIGS. 3A-B is composed of a single layer 40 of material having the ribbon-like configuration. The single layer 40 of material may be a porous and/or permeable, as for example, a layer 40 formed of a plurality of braided wires 50 or weaved filaments 50' (FIG. 5A), a mesh 55 (FIG. 5B), and/or a layer 40 of material having perforations 57 (FIG. 5C), or the like or combinations thereof. The wires 50 and/or filaments 50' are composed of biocompatible metallic and/or polymeric materials, alloys or combinations thereof. For example, one or more wires 50 may have a platinum core with a respective outer layer of Nitinol. In some embodiments, the elongate flat member 100 comprises a single layer, flat ribbon braid. When the elongate flat member 100 is braided, woven or mesh, the proximal end 142 and/or distal end 122 may be secured, having the plurality of wires 50 attached or coupled to each other, or to another element (e.g., a cap, non-traumatic tip, or the like) at the respective proximal end 142 and/or distal end 122 via adhesive, clamping, or the like, as shown at the distal end 122 in FIG. 6A. Alternatively, the proximal end 142 and/or distal end 122 of the elongate flat member 100 may be unsecured, having the plurality of wires 50 at the respective proximal end 142 and/or distal end 122 lose and free, as shown at the distal end 122 in FIG. 6B. Further, a coil 123 may be coupled to the secured proximal end 142 and/or distal end 122 the elongate flat member 100, as shown at the distal end 122 in FIG. 6C. The coil 123 may be composed of shape memory material and may assume a loop like configuration, such as the loops 12 of the embolic device 10, when the embolic device 10 is in the three-dimensional unconstrained configuration. The shape memory material for the coil 123 may be composed of Platinum Group metals, such as, platinum, rhodium, palladium, rhenium, as well as tungsten, gold, silver, tantalum, and alloys of these metals, such as platinum/tungsten alloy, gold/platinum alloy, or the like and combinations thereof. The coil 123 when disposed at the distal end 122 of the elongate flat member 100 may be configured to lead the embolic device when deployed within an aneurysm 20.

In some embodiments, the elongate flat member 100 comprises a braid that is formed out of one or more braid members, and the one or more braid members are metallic filaments or wires.

In further embodiments, the single layer 40 of material may be a non-porous or impermeable layer of material (e.g., solid), as shown in FIG. 3A. It should be appreciated that the single layer 40 of the elongate flat member 100 may include one or more materials, alloys of combinations thereof.

In other embodiments, the elongate flat member 100 may be composed of a plurality of layers 42 (e.g., FIG. 7A); the layers may be porous/permeable, non-porous/impermeable and/or include one or more materials, as described above, or combinations thereof. The elongate flat member 100 composed of a plurality of layers 42 may have the flat-ribbon configuration of FIG. 3A. By way of non-limiting example, the elongate flat member 100 may include a tubular member 150, as shown in FIG. 7A, the tubular member 150 may include a braid or mesh that is flattened forming a similar flat-ribbon configuration of FIG. 3A, such as a flattened tubular braid, as shown in FIG. 7B. The tubular member 150 when flattened into the ribbon-like configuration includes at least two layers 42, as shown in FIG. 7B. In another exemplary embodiment, the elongate flat member 100 may be composed of a cylindrical member 160, as shown in FIG.

8A, that is flattened forming a similar flat-ribbon configuration of FIG. 3A, as shown in FIG. 8B. The cylindrical member 160 may be composed of one or more materials or combinations thereof. The cylindrical element 160 of FIGS. 8A-B may further include a core 162 and an outer layer 164. By way of non-limiting example, the core 162 may be composed of platinum and the outer layer 164 may be composed of Nitinol.

It should be appreciated that the elongate flat member 100 can be woven from wires, cut out of tubes, or cut out of sheets using a variety of techniques, including laser cutting or etching a pattern onto a tube or sheet, or other suitable techniques. It should be further appreciated that other suitable configurations of the elongate flat member 100 may be considered for the manufacturing of the embolic device 10.

Referring back to FIG. 3A, the elongate flat member 100 comprises a length $L_1$ than rages from approximately 2 to 40 centimeters, and in some embodiments the $L_1$ ranges from approximately 5 to 25 centimeters. The elongate flat member 100 further comprises a width $W_1$ that ranges from approximately 0.5 to 10 millimeters, and in some embodiments the $W_1$ ranges from approximately 1 to 3 millimeters. Additionally, the elongate flat member 100 comprises a thickness $T_1$ that ranges from approximately 0.05 to 0.75 millimeters, and in some embodiments the $T_1$ ranges from approximately 0.1 to 0.4 millimeters. In some embodiments, the one or more dimension ($L_1$, $W_1$, or $T_1$) of the elongate flat member 100 remain constant throughout the element 100, such as having the same dimension from the proximal portion 140 to the distal portion 120. In other embodiments, the one or more dimension ($L_1$, $W_1$, or $T_1$) of the elongate flat member 100 may varied, having different dimension along the length of the elongate flat member 100 (e.g., tapered configuration).

The elongate flat member 100 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol. Certain super-elastic alloys may be desirable for their shape recoverable features, which tolerate significant flexing without deformation even when used in small dimensioned elongate flat member 100. Further when the embolic device 10 comprises an elongate flat member 100 composed of self-expanding materials, the unconstrained embolic device 10 is biased to expand into the predetermined deployed configuration, which will be described in further detail below. Some super-elastic alloys include nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum).

The elongate flat member 100 may include radio-opaque markers or be coated with a layer of radiopaque materials. Additionally, the elongate flat member 100 may carry and/or the surfaces of the elongate flat member 100 may be coated with a bioactive or therapeutic agent (e.g., thrombosis inducing agent).

Further suitable metals and alloys for the elongate flat member 100 include the Platinum Group metals, such as, platinum, rhodium, palladium, rhenium, as well as tungsten, gold, silver, tantalum, and alloys of these metals, such as platinum/tungsten alloy, or the like and combinations thereof. These metals have significant radiopacity and in their alloys may be tailored to accomplish an appropriate blend of flexibility and stiffness.

Figure 9:
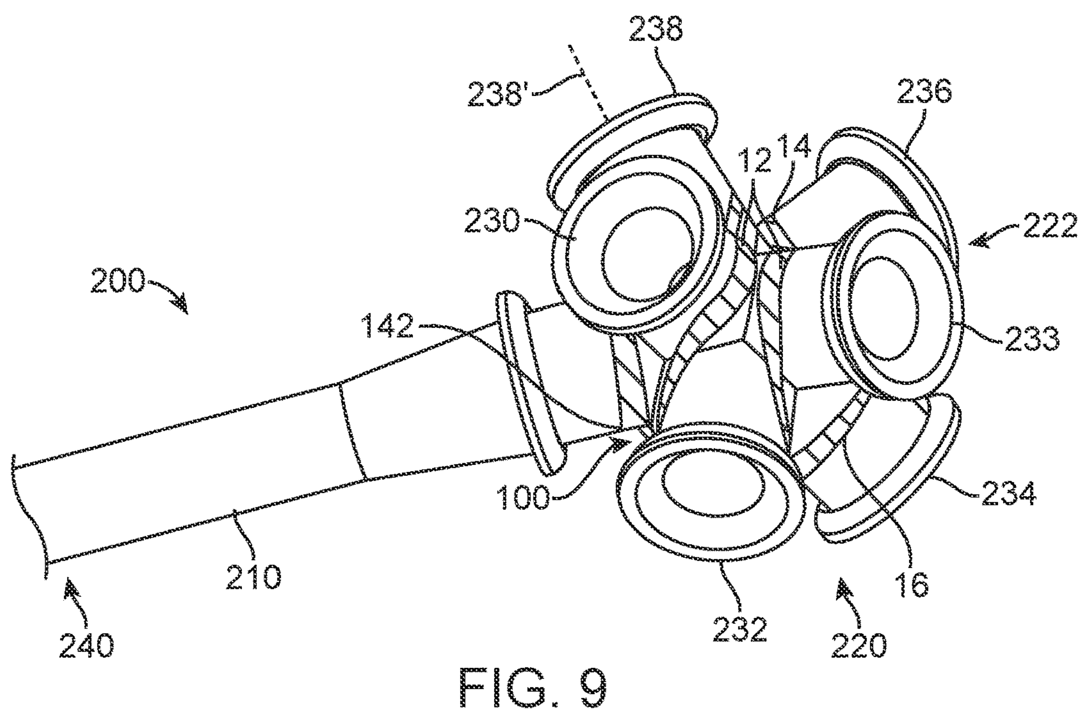
FIG. 9 is a perspective view of the elongate flat member of FIG. 3A in a mandrel for manufacturing the embolic device of FIG. 1, according to embodiments of the disclosed inventions.

FIG. 9 illustrate the embolic device 10 of FIG. 1 comprising the elongate flat member 100 and being manufactured using a mandrel 200, according to the embodiments of the disclosed inventions. The elongate flat member 100 is disposed on a mandrel 200. The mandrel 200 comprises a handle post 210 extending from a proximal portion 240 to a distal portion 220. The distal portion 220 of the mandrel 200 comprises a plurality of extending posts 230, 232, 233, 234, 236 and 238. The handle post 210 and the laterally extending posts 230, 232, 233, 234, 236 and 238, comprise cylindrical or tubular configurations having rounded cross-sections. Alternative, the handle post 210 and the laterally extending posts 230, 232, 233, 234, 236 and 238, may comprise any other suitable configuration, such as, for example having elliptical cross-sections. The extending posts 230, 232, 233, 234, 236 and 238 extends outward from the handle post 210 distal portion 220, and are circumferentially disposed around the handle post 210 distal portion 220. Each of the extending post 230, 232, 233, 234, 236 and 238 comprises a respective center point (e.g., 238'), in which each extending post is disposed at a suitable degree (e.g., approximately between 65 to 95 degrees) relative to the adjacent post center point, as shown in FIG. 9. In alternative embodiments, the mandrel 200 may comprise four extending posts, in which each extending post is disposed at approximately 90 degrees relative to the adjacent post center point (not shown). It should be appreciated that the mandrel 200 may comprise any number of extending posts, any number of angles between the extending post (e.g., the posts may be symmetrically or not-symetrically disposed between each other), or any other suitable configuration for the manufacturing of the embolic device 10, such as for example the mandrel 200' of FIG. 10. The mandrel 200' of FIG. 10 includes a flat base 240 and a plurality of extending posts 250, 251, 252, 253, 254, 255, and 256 extending outwardly from the base 240.

Figure 10:
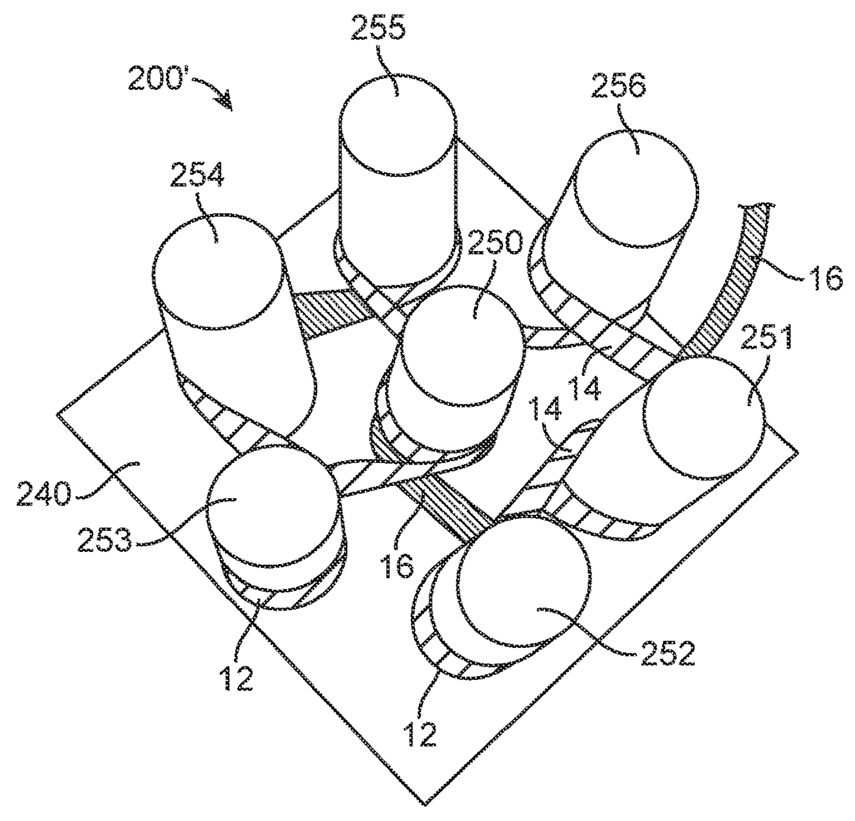
FIG. 10 is a perspective view of the elongate flat member of FIG. 3A in another mandrel for manufacturing the embolic device of FIG. 1, according to embodiments of the disclosed inventions.

The elongate flat member 100 is disposed on the mandrel 200 by laying the elongate flat member 100, particularly one of either, the first side surface 14 or the second side surface 16 against the mandrel 200. For example, when the first side surface 14 of the elongate flat member 100 is laid against, disposed on, or in contact with the mandrel 200, the second side surface 16 is exposed and visible to the technician manufacturing the embolic device 10 (i.e., not contacting the mandrel 200), not shown. Conversely, when the second side surface 16 of the elongate flat member 100 is laid against, disposed on or in contact with the mandrel 200, the first side surface 14 of the elongate flat member 100 is exposed and visible to the technician manufacturing the embolic device 10 (i.e., not contacting the mandrel 200) as shown in FIGS. 9 and 10.

In the three-dimensional unconstrained configuration of the embolic device 10, the elongate flat member 100 assumes a plurality of successive loops 12 in which the elongate flat member 100 is at least partially twisted about its longitudinal axis between each loop of the plurality, so that the first side surface 14 faces externally of each loop 12, and the second side surface 16 faces an interior of each loop 12, respectively, regardless of a change in direction and/or orientation of the elongate flat member 100. The three-dimensional unconstrained configuration of the embolic device 10 is set by disposing and wrapping the elongate flat member 100 in the mandrel (e.g., FIGS. 9 and 10) forming a plurality of successive loops 12, by at least partially twisting the elongate flat member 100 about its longitudinal axis between each post of the mandrel forming each loop of the plurality, so that the first side surface 14 faces externally of each post and/or loop, and the second side surface 16 faces an interior of each loop and is at least in partial contact with each post, respectively, regardless of a change in direction and/or orientation of the elongate flat member 100, as shown in FIGS. 9 and 10.

Figure 11:
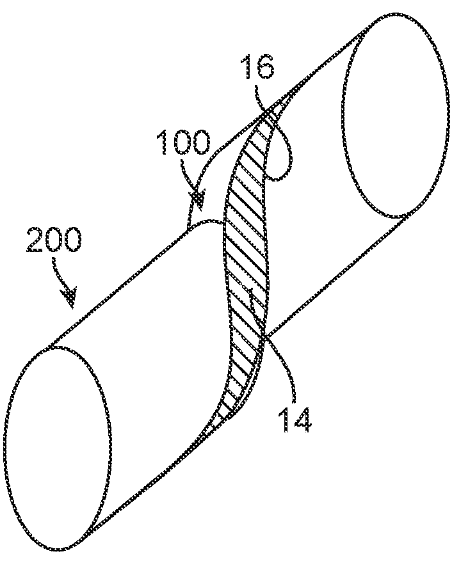
FIG. 11 is a perspective view of a partial twist of the elongate flat member according to the embodiments of FIGS. 9 and 10.

In the embodiments of the disclosed inventions, the at least partial twist of the elongate flat member 100 about its longitudinal axis between each loop and/or between each post is depicted in detail in FIG. 11. The partial twist is approximately 120° about the longitudinal axis elongate flat member 100, so that that the first side surface 14 of the elongate flat member 100 faces externally of each loop 12, and the second side surface 16 elongate flat member 100 faces an interior of each loop, respectively, regardless of a change in direction and/or orientation of the elongate flat member 100 when the embolic device 10 is in the three-dimensional unconstrained configuration, as shown in FIGS. 1 and 2B. It should be appreciated that the partial twist may include other suitable degrees about the longitudinal axis elongate flat member 100, as long as, one of the side surface (e.g., first side surface 14) of the elongate flat member 100 faces externally of each loop 12, and the reversed side surface (e.g., second side surface 16) of the elongate flat member 100 faces an interior 11 of each loop 12, respectively, regardless of a change in direction and/or orientation of the elongate flat member 100 in the three-dimensional unconstrained configuration of the embolic device 10.

Further, a degree of twist between successive loops 12 can be expressed as a pitch where there is an amount of twist angle per unit length. The twist pitch is preferably related to the diameter of the adjacent loops 12 wherein the pitch is about 1 to 2 times 360°/π D, where D is the average curve diameter of the adjacent loops 12. The twist pitch may vary from approximately 0.25 to approximately 4 times (360°/π D), and in some embodiments, the twist pitch may vary from approximately 0.75 to approximately 2.5 times (360°/π D). In one embodiment, the twists of the elongate flat member 100 forming the three-dimensional unconstrained configuration of the embolic device 10 generally occur with a constant cross-section of the elongate flat member 100 throughout the twists. Alternatively, the twists may occur where the cross-section of the elongate flat member 100 changes throughout the twist.

Figure 12:
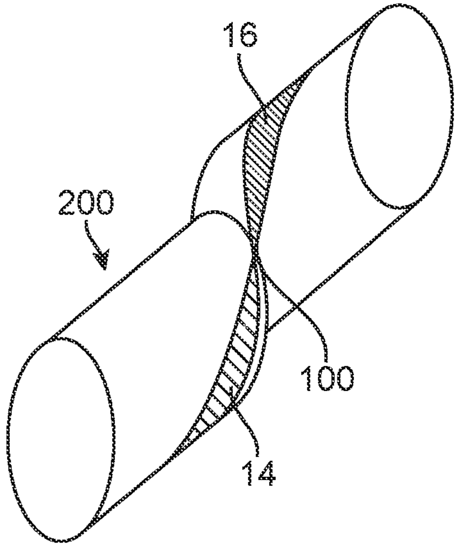
FIG. 12 is a perspective view of a twist of an elongate flat member for illustration purposes.

For illustration purposes, FIG. 12 depicts an undesirable partial twist of the elongate flat member 100 about its longitudinal axis (e.g., 60°) between each loop and/or between each post, since this twist will cause first side surface 14 of the elongate flat member 100 to face externally and internally in alternating loops, and the second side surface 16 elongate flat member 100 to also face externally and internally in alternating loops.

The steps of disposing, laying, wrapping and/or twisting the elongate flat member 100 on the mandrel 200, according to the disclosed inventions, will be described in further detail below. After the elongate flat member 100 is disposed on the mandrel 200 forming the three-dimensional configuration of the embolic device 10, the embolic device 10 is thermally treated while the elongate flat member 100 is wound in alternating directions about respective posts extending outwardly from the mandrel to thereby form the plurality of successive loop 12. The three-dimensional unconstrained configuration of the embolic device 10 is imparted by thermally treating elongate flat member 100 as described above, so that the device 10 is biased to assume the three-dimensional unconstrained configuration, as shown in FIGS. 1 and 2B. The mandrel 200 is composed of materials having sufficient heat resistance to allow the heat treatment of the embolic device 10. The mandrel 200 usually comprises refractory material such as alumina or zirconia, or any other suitable heat resistant material.

Figure 13:
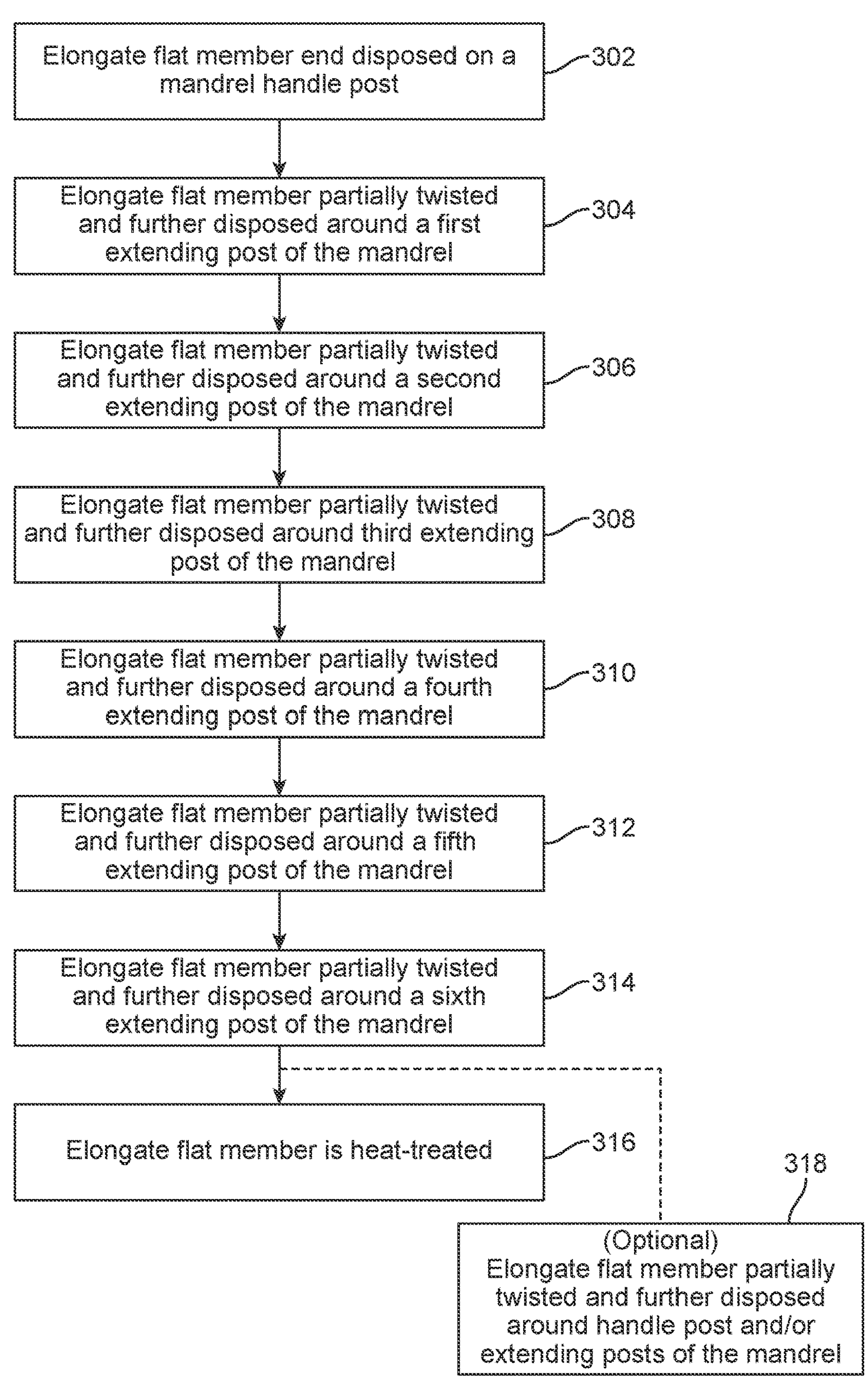
FIG. 13 is a schematic view of the method of manufacturing the embolic device of FIG. 1, according to embodiments of the disclosed inventions.

FIG. 13 depicts a manufacturing method 300 of the embolic device 10 using the above described elongate flat member 100 and mandrel 200, according to the embodiments of the disclosed inventions.

In step 302, either the proximal end 142 or the distal end 122 of the elongate flat member 100 is first disposed on the mandrel 200, so that either the first surface 14 or the second surface 16 is in contact with the mandrel 200. By way of non-limiting example, the proximal end 142 of the elongate flat member 100 is laid against the handle post 210 disposed proximately to the extending posts 230, 232, 233, 234, 236 and 238, having a portion of the second side surface 16 in contact with the mandrel 200, as shown in FIG. 9.

In step 304, the elongate flat member 100 is partially twisted about its longitudinal axis and further disposed around a first extending post forming a loop so that the first side surface faces externally, (e.g., away from the post), and the second side surface faces internally (e.g., towards or in partial contact with the post). For example, the elongate flat member 100 is extended so as to partially twist and wrap around the first extending post 230 in a clockwise direction having a portion of the second side surface 16 in contact with the extending post 230, as shown in FIG. 9.

In step 306, the elongate flat member 100 is partially twisted about its longitudinal axis and further disposed around a second extending post forming a loop so that the first side surface faces externally, (e.g., away from the post), and the second side surface faces internally (e.g., towards or in partial contact with the post). As shown in FIG. 9, the elongate flat member 100 is extended so as to partially twist and wrap around the second extending post 232 in a counter-clockwise direction having a portion of the second side surface 16 in contact with the extending post 232.

In step 308, the elongate flat member 100 is partially twisted about its longitudinal axis and further disposed around a third extending post forming a loop so that the first side surface faces externally, (e.g., away from the post), and the second side surface faces internally (e.g., towards or in partial contact with the post). As shown in FIG. 9, the elongate flat member 100 is extended so as to partially twist and wrap around the third extending post 233 in a clockwise direction having a portion of the second side surface 16 in contact with the third extending post 233.

In step 310, the elongate flat member 100 is partially twisted about its longitudinal axis and further disposed around a fourth extending post forming a loop so that the first side surface faces externally, (e.g., away from the post), and the second side surface faces internally (e.g., towards or in partial contact with the post). As shown in FIG. 9, the elongate flat member 100 is extended so as to partially twist and wrap around the fourth extending post 234 in a counter-clockwise direction having a portion of the second side surface 16 in contact with the extending post 234.

In step 312, the elongate flat member 100 is partially twisted about its longitudinal axis and further disposed around a fifth extending post forming a loop so that the first side surface faces externally, (e.g., away from the post), and the second side surface faces internally (e.g., towards or in partial contact with the post). For example, the elongate flat member 100 is extended so as to partially twist and wrap around the fifth extending post 236 in a clockwise direction having a portion of the second side surface 16 in contact with the extending post 236, as shown in FIG. 9.

In step 314, the elongate flat member 100 is partially twisted about its longitudinal axis and further disposed around a sixth extending post forming a loop so that the first side surface faces externally, (e.g., away from the post), and the second side surface faces internally (e.g., towards or in partial contact with the post). As shown in FIG. 9, the elongate flat member 100 is extended so as to partially twist and wrap around the sixth extending post 238 in a counter-clockwise direction having a portion of the second side surface 16 in contact with the extending post 238.

In step 316, the elongate flat member 100 is heat treated providing the three-dimensional unconstrained configuration of the embolic device 10, as shown in FIGS. 1 and 2B.

In an optional step 318 prior to step 316, the elongate flat member 100 may be further partially twisted and disposed around handle post and/or extending posts in alternating clockwise and counter-clockwise directions having a surface of the elongate flat member 100 in at least a partial contact with the extending posts and handle post.

It should be appreciated that in the steps 302 to 316, the transitions of the elongate flat member 100 from one post to another post of the mandrel 200 are discrete, in a wave-like fashion, allowing one of the side surfaces (e.g., 16) of the elongate flat member 100 to at least partially contact the mandrel 200 while the opposite side surface (e.g., 14) is free, visible or exposed (i.e., not contacting the mandrel 200).

The embolic device 10 resulting from the above described manufacturing steps comprises a three-dimensional unconstrained configuration having a plurality of successive loops in which the elongate flat member 100 is at least partially twisted about its longitudinal axis between each loop of the plurality, so that the first side surface 14 faces externally of each loop, and the second side surface 16 faces an interior of each loop, respectively, regardless of a change in direction and/or orientation of the elongate flat member, as shown in FIGS. 1 and 2B. The side surface of the elongate flat member 100 that was disposed on the mandrel 200 during the manufacturing steps (e.g., surface 16) faces the interior 11 of each loop 12 (e.g., concave portions), while the side surface of the elongate flat member 100 that was not contacting the mandrel 200 during the manufacturing steps (e.g., surface 14) faces the exterior of each loop 12 (e.g., convex portion) of the embolic device 10 in the three-dimensional unconstrained configuration, as shown in FIGS. 1 and 2B.

The features of the embolic device 10 three-dimensional unconstrained configuration provide several important advantages, for example for use as an embolic device intended for small-diameter site, such as a neurovascular aneurysm. First, the embolic device 10 can be forced into a highly compressed or contracted state with relatively little bending or stress since the embolic device 10 comprises discrete transition areas (e.g., loops, partial twists). This contrasts with embolic devices having sharp twists, bends or turns causing packing inefficient and inability to be compressed tightly due to its relatively rough transition areas. Similarly, the stress on embolic devices having sharp twists, bends or turns, overlapping sections may create more contact points and friction of the embolic device with the delivery system, particularly during movement through a tortuous vascular path, having undesirable effects (e.g., slower deployment of the embolic devices, embolic device metal fatigue, or the like).

Further, when the embolic device 10 is being deployed through a delivery catheter 80 into the aneurysm 20, and assumes the three-dimensional unconstrained configuration after being deployed out of the delivery catheter 80 within the aneurysm (FIGS. 2A-B), the elongate flat member 100 assumes a plurality of successive loops 12 in which the elongate flat member 100 is at least partially twisted about its longitudinal axis between each loop 12 of the plurality, so that the first side surface 14 faces externally of each loop 12 towards an interior wall 22 of the aneurysm 20, and the second side surface 16 faces an interior 11 of each loop, respectively, regardless of a change in direction and/or orientation of the elongate flat member 100, so that the first side surface 14 of the device 10 engages and contacts the interior wall 22 of the aneurysm 20 without distending the sac or having any sharp turns or angles that may cause damage or rupture of the aneurysm interior wall 22.

It should be appreciated that the embolic device 10 constructed according to the disclosed inventions may be deployed into the target site by methods known in the art.

Although particular embodiments have been shown and described herein, it will be understood by those skilled in the art that they are not intended to limit the present inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A method of manufacturing an embolic device, the method comprising:

providing a mandrel having a plurality of extending posts;

providing an elongate flat member having a longitudinal axis, a first side comprising a first side surface, and a second side comprising a second side surface, the first and second sides being reverse to each other with the first side surface and second side surface facing in opposite directions, the elongate flat member having an elongated constrained configuration for being deployed through a delivery catheter to a targeted vascular site;

winding the flat member at least partially around a first extending post of the plurality of extending posts such that the second side surface of the flat member is in contact with the first extending post and the first side surface faces away from the first extending post;

partially twisting the flat member about its longitudinal axis as it extends from the first extending post to a second extending post of the plurality of extending posts and winding the flat member at least partially around the second extending post such that the second side surface of the flat member is in contact with the second extending post and the first side surface faces away from the second extending post; and heat treating the elongate flat member while wound on the mandrel to provide a three-dimensional unconstrained configuration to the flat member comprising a plurality of successive loops in which the elongate flat member is at least partially twisted about its longitudinal axis between each loop of the plurality of loops.

2. The method of claim 1, wherein the elongate flat member has a three-dimensional unconstrained configuration in which the first side surface faces externally of each loop, and the second side surface faces an interior of each loop, respectively, regardless of a change in direction and/or orientation of the elongate flat member, and wherein loops that are directly adjacent to a first loop of the plurality of successive loops have respective rotational axes which are angled to a rotational axis of the first loop by 65-95 degrees.

3. The method of claim 1, wherein the flat member is wound around the extending posts in alternating clockwise and counter-clockwise directions.

4. The method of claim 1, further comprising:

after winding the flat member at least partially around the second extending post, partially twisting the flat member about its longitudinal axis as it extends from the second extending post to a third extending post of the plurality of extending posts and winding the flat member at least partially around the third extending post such that the second side surface of the flat member is in contact with the first extending post and the first side surface faces away from the first extending post;

partially twisting the flat member about its longitudinal axis as it extends from the third extending post to a fourth extending post of the plurality of extending posts and winding the flat member at least partially around the fourth extending post such that the second side surface of the flat member is in contact with the first extending post and the first side surface faces away from the first extending post;

partially twisting the flat member about its longitudinal axis as it extends from the fourth extending post to a fifth extending post of the plurality of extending posts and winding the flat member at least partially around the fifth extending post such that the second side surface of the flat member is in contact with the first extending post and the first side surface faces away from the first extending post; and partially twisting the flat member about its longitudinal axis as it extends from the fifth extending post to a sixth extending post of the plurality of extending posts and winding the flat member at least partially around the fifth extending post such that the second side surface of the flat member is in contact with the first extending post and the first side surface faces away from the first extending post.

5. The method of claim 4, wherein the flat member is wound around the extending posts in alternating clockwise and counter-clockwise directions.

6. The method of claim 1, wherein the flat member is laid against a handle of the mandrel and partially twisted about its longitudinal axis as the flat member extends to the first extending post.

7. The method of claim 1, wherein the flat member is composed of a metal selected from the group consisting of: a Platinum Group metal, rhenium, tungsten, gold, silver and tantalum, and an alloy of any of the foregoing metals.

8. The method of claim 7, wherein the Platinum Group metal is selected from the group consisting of platinum, rhodium, and palladium, and wherein the alloys of the foregoing metals is selected from the group consisting of an alloy of platinum, an alloy of rhodium, an alloy of palladium, an alloy of rhenium, an alloy of tungsten, an alloy of gold, an alloy of silver, and an alloy of tantalum.

9. The method of claim 1, wherein the flat member comprises a braided mesh formed of a plurality of filaments or wires.

10. The method of claim 9, wherein the filaments or wires are attached to each other or to a respective securing element at each of a proximal end and a distal end of the braided mesh.

11. The method of claim 10, wherein the filaments or wires are attached to each other via an adhesive at each of the proximal and distal ends of the braided mesh.

12. The method of claim 11, further comprising:

coupling a respective coil to one or both of a proximal end and a distal end of the flat member.

13. The method of claim 12, wherein the respective coil(s) are composed of shape memory material and assume a plurality of successive loops when the braided mesh is in the three-dimensional unconstrained configuration.

14. The method of claim 1, wherein the elongate flat member comprises a braided mesh formed of a plurality of filaments or wires and the filaments or wires are attached to a respective securing element at each of a proximal end and a distal end of the braided mesh.

15. The method of claim 14, wherein each respective securing element is selected from the group consisting of: a cap, and a non-traumatic tip.

16. A method of manufacturing an embolic device, the method comprising:

providing a mandrel having a plurality of extending posts;

providing an elongate flat member having a longitudinal axis, the flat member having a ribbon-like structure having a width significantly exceeding its thickness, a first side comprising a first side surface, and a second side comprising a second side surface, the first and second sides being reverse to each other with the first side surface and second side surface facing in opposite directions, the elongate flat member having an elongated constrained configuration for being deployed through a delivery catheter to targeted vascular site;

winding the flat member at least partially around a first extending post of the plurality of extending posts such that the second side surface of the flat member is in contact with the first extending post and the first side surface faces away from the first extending post;

partially twisting the flat member about its longitudinal axis about 120° as it extends from the first extending post to a second extending post of the plurality of extending posts and winding the flat member at least partially around the second extending post such that the second side surface of the flat member is in contact with the second extending post and the first side surface faces away from the second extending post; and heat treating the elongate flat member while wound on the mandrel to provide a three-dimensional unconstrained configuration to the flat member comprising a plurality of successive loops in which the elongate flat member is at least partially twisted about its longitudinal axis between each loop of the plurality of loops.

17. The method of claim 16, wherein the elongate flat member has a three-dimensional unconstrained configuration in which the first side surface faces externally of each loop, and the second side surface faces an interior of each loop, respectively, regardless of a change in direction and/or orientation of the elongate flat member, and wherein loops that are directly adjacent to a first loop of the plurality of successive loops have respective rotational axes which are angled to a rotational axis of the first loop by 65-95 degrees.

18. The method of claim 16, wherein the flat member is wound around the extending posts in alternating clockwise and counter-clockwise directions.

19. The method of claim 16, further comprising:

after winding the flat member at least partially around the second extending post, partially twisting the flat member about its longitudinal axis as it extends from the second extending post to a third extending post of the plurality of extending posts and winding the flat member at least partially around the third extending post such that the second side surface of the flat member is in contact with the first extending post and the first side surface faces away from the first extending post;

partially twisting the flat member about its longitudinal axis as it extends from the third extending post to a fourth extending post of the plurality of extending posts and winding the flat member at least partially around the fourth extending post such that the second side surface of the flat member is in contact with the first extending post and the first side surface faces away from the first extending post;

partially twisting the flat member about its longitudinal axis as it extends from the fourth extending post to a fifth extending post of the plurality of extending posts and winding the flat member at least partially around the fifth extending post such that the second side surface of the flat member is in contact with the first extending post and the first side surface faces away from the first extending post; and partially twisting the flat member about its longitudinal axis as it extends from the fifth extending post to a sixth extending post of the plurality of extending posts and winding the flat member at least partially around the fifth extending post such that the second side surface of the flat member is in contact with the first extending post and the first side surface faces away from the first extending post.

20. The method of claim 19, wherein the flat member is wound around the extending posts in alternating clockwise and counter-clockwise directions.

* * * * *